| United States Patent [19] | [11] Patent Number: 4,782,145 |
| Brighty et al. | [45] Date of Patent: Nov. 1, 1988 |

[54] PROCESS FOR PENEM DERIVATIVES

[75] Inventors: Katherine E. Brighty, Groton; David L. Lindner, Niantic, both of Conn.

[73] Assignee: Pfizer Inc., New York, N.Y.

[21] Appl. No.: 869,760

[22] Filed: Jun. 2, 1986

[51] Int. Cl.[4] ................. C07D 499/04; A61K 31/425
[52] U.S. Cl. ..................................... 540/214; 540/310
[58] Field of Search ............... 540/310, 214; 514/210, 514/192, 193

[56] References Cited

U.S. PATENT DOCUMENTS

| 4,530,793 | 7/1985 | Girijavallabhan | 540/310 |
| 4,585,874 | 4/1986 | Alpegiani et al. | 540/214 |
| 4,675,396 | 6/1987 | Ross et al. | 540/310 |
| 4,695,626 | 9/1987 | Brighty | 540/214 |

OTHER PUBLICATIONS

Leanza et al., Tetrahedron, 39, pp. 2505–2513 (1983).
Ganguly et al., Journal of Antimicrobial Chemotherapy, 9, Suppl. C, pp. 1–6 (1982).

*Primary Examiner*—Nicholas S. Rizzo
*Attorney, Agent, or Firm*—Peter C. Richardson; J. Trevor Lumb; Robert K. Blackwood

[57] ABSTRACT

An efficient process for converting readily available 4-acetoxy-2-azetidinones to allyl 2-thioxopenam-3-carboxylates, intermediates useful for the synthesis of penem antibiotics.

24 Claims, No Drawings

PROCESS FOR PENEM DERIVATIVES

BACKGROUND OF THE INVENTION

The present invention concerns an improved process and certain intermediates useful for the synthesis of compounds of the formula

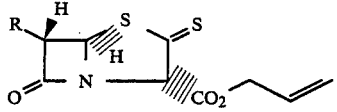  (I)

where R is hydrogen or

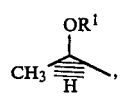

and $R^1$ is a conventional hydroxy protecting group, particularly t-butyldimethylsilyl. These compounds are of known utility as intermediates in the synthesis of known valuable penem antibiotics and/or beta-lactamase inhibitors such as Sch 29482:

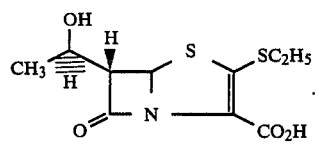

See Ganguly et al., J. Antimicrob. Chemotherapy. 9, Supplement C, pp. 1-6 (1982).

The present intermediate compound wherein R is 1-(t-butyldimethylsilyloxy)ethyl is a known compound [Leanza et al., Tetrahedron 39, pp. 2505-2513 (1983)]. The present intermediates are converted to known, valuable penems (e.g. Ganguly et al., loc. cit., Hamanaka, European Patent Application 130,025; Daniels et al., J. Chem. Soc., Chem. Commun. 1982, pp. 1119-1120; Tanaka et al., ibid., pp. 713-714) according to known methods of alkylation (e.g. Leanza et al., loc. cit.), removal of allyl protecting groups (e.g., Ganguly et al., loc. cit.; Girijavallabhan et al., Tetrahedron Lett. 22, pp. 3485-3488 (1981), Jeffrey et al., J. Org. Chem. 47, pp. 587-590 (1982), and removal of silyl protecting groups [e.g., Hayashi et al., Chem. Pharm. Bull. 29, pp. 3158-3172 (1981)].

SUMMARY OF THE INVENTION

Attractive precursors for the above compounds of the formula (I) are the 4-acetoxy-2-azetidinones of the formula

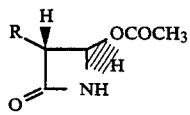  (A)

where R is as defined above. Indeed, the racemic compound wherein R is H is now available commercially [See Mickel, Aldrichimica Acta. 18, pp. 95-99 (1985)], and the chiral compound wherein R is 1-(t-butyldimethylsilyloxy)ethyl is readily available from 6-aminopenicillanic acid by the method of Leanza et al., loc. cit.

According to the present invention, the compounds of the formula (A) are first reacted with sodium t-butyl trithiocarbonate and then with allyl glyoxylate to form a compound of the formula

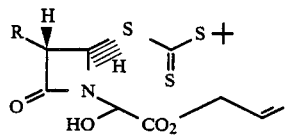  (B)

and then with $SOX_2$ (where X=Cl or Br) to form a compound of the formula

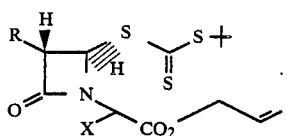  (III)

The present invention is specifically directed to the unconventional process step of converting a compound of the formula (III) to a compound of the formula

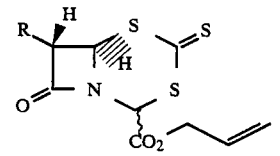  (II)

which comprises either:

(a) contacting said compound of the formula (III) with sodium iodide in a reaction inert solvent at 0°-35° C.; or (b) warming said compound of the formula (III) in a reaction inert solvent, at 25°-80° C. when X is bromo or at 60°-100° C. when X is chloro. The preferred solvent comprises acetonitrile, with or without additional reaction inert solvent(s).

As used herein, the expression 'reaction inert solvent' refers to a solvent which does not interact with reactants, intermediates or products in a manner which adversely affects yield. It should be noted that in the reaction of the preceding paragraph, carbonium ion trapping solvents such as acetonitrile, which can have a favorable effect on yield by reducing side reactions, would still be considered reaction inert according to this definition.

The present invention is also directed to the unconventional process step of converting a compound of the formula (II) to a compound of the formula (I), comprising contacting said compound (II) with substantially one equivalent of a strong, anhydrous base of low nucleophilicity in a reaction inert solvent, and to the intermediate compounds of the formula (II) per se.

In all cases R is as defined above for the compound of the formula (I). Preferred values of R are hydrogen [with the compounds (A), (B), (III), (II) and (I) in racemic form], and 1-(t-butyldimethylsilyloxy)ethyl (with the corresponding compounds in optically active form).

A 'strong base of low nucleophilicity' refers to such bases as an alkali metal hydride, t-butoxide or hexamethyldisilazide, of sufficient strength to lead to the desired reaction with little or no undesired interaction with the beta-lactam or allyl ester groups. The reaction is optionally carried out in the presence of triphenylphosphine.

DETAILED DESCRIPTION OF THE INVENTION

The present invention is readily carried out. The starting materials of the formula (II) are prepared by conventional methods, as exemplified in Preparations detailed below.

When X is chloro or bromo, the conversion of the compound (III) to the compound (II) is carried out by dissolving the compound (III) in a reaction inert solvent, preferably acetonitrile at 0°–35° C., conveniently at an ambient temperature of about 18°–25°, contacting the solution with an iodide salt, conveniently sodium iodide, and allowing the reaction to proceed substantially to completion (about 0.3 to 1 hour at ambient temperature when a stoichiometric amount of iodide salt is used). Alternatively, the compound (III) is simply warmed in a reaction inert solvent, preferably acetonitrile, with or without the presence of a further reaction inert solvent, at 25°–80° C. when X is bromo and at 60°–100° C. when X is chloro. In either case, the product is isolated and purified by conventional methods, e.g. dilution with a water immiscible organic solvent, removal of salts and other impurities by water extraction, and evaporation, with optional column chromatography on silica gel.

The compound (II) is converted to the compound (I) in a reaction-inert solvent in the presence of substantially one equivalent of a strong, anhydrous base of low nucleophilicity. Temperature is not highly critical, but is preferably in the range of −50° to 10° C. to minimize side reactions; most preferred are temperatures in the mid to upper portion of the range, e.g., near 0° C. Solvent is not critical, although polar ethers such as tetrahydrofuran are preferred. The reaction is preferably carried out in the presence of substantially one equivalent of triphenylphosphine, in which case the sulfur extruded in the reaction ends up as triphenylphosphine sulfide. Preferred strong bases of low nucleophilicity, as defined above, are sodium hydride, potassium t-butoxide, lithium t-butoxide and lithium hexamethyldisilazide.

As noted above, the present compounds (I) are converted to known and valuable penems by conventional methods well known in the beta-lactam art.

The present invention is illustrated by the following examples. However, it should be understood that the invention is not limited to the specific details of these examples.

EXAMPLE 1

Allyl 4-Thioxo-1-aza-3,5-dithiabicyclo-[4.2.0]octan-8-one-2-carboxylate

Method A

To a solution of the product of Preparation 4 (0.04 g., 0.11 mmol) in 2 ml. CH$_3$CN was added NaI (17.9 mg.). After stirring 30 minutes, the reaction mixture was stripped to an oil which was distributed between 2 ml. each of water and CH$_2$Cl$_2$. The CH$_2$Cl$_2$ layer was separated and chromatographed on silica gel using 1:2 ethyl acetate:hexane as eluant to yield title product as an oil, 9.7 mg.; tlc Rf 0.3 (1:2 ethyl acetate:hexane); $^1$H-nmr (CDCl$_3$) delta (ppm) 5.98–5.82 (m, 1H), 5.86 (s, 1H), 5.49 (dd, J=4.5, 1.7, 1H), 5.41–5.31 (m, 2H), 4.70 (d, J=5.9, 2H), 3.83 (dd, J=15.6, 4.5, 1H), 3.25 (dd, J=15.5, 1.8, 1H).

Method B

A solution of the product of Preparation 4 (515 mg., 1.4 mmol) in 14 ml. CH$_3$CN was refluxed from an oil bath at 90° C. for 16 hours, then stripped and the residue chromatographed on silica gel with 5:2 hexane:ethyl acetate as eluant to yield title product, 253 mg.; tlc Rf as in Method A above.

Method C

The product of Preparation 5 (9.3 mg., 0.023 mmol) was warmed in 1 ml. CH$_3$CN at 60°–62° C. for 40 minutes, then stripped and chased with ethyl acetate and finally CH$_2$Cl$_2$ to yield an essentially quantitative weight of title product, identical with the product of Method A.

EXAMPLE 2

Allyl (r-5H)-3-Thioxo-1-aza-4-thiabicyclo[3.2.0]heptan-7-one-c-2-carboxylate or Allyl 2-Thioxopenam-3-carboxylate Method A Sodium hydride (60% in mineral oil, 60.3 mg., 1.5 mmol) was suspended in 1 ml. tetrahydrofuran. Title product of the preceding Example (16.7 mg., 0.06 mmol) dissolved in 1 ml. tetrahydrofuran was added to the suspension over 1–2 minutes. A transient purple color followed by a yellow color and gas evolution was noted After 10 minutes, triphenylphosphine (18.1 mg., 0.069 mmol) was added. After a further 10 minutes, the reaction mixture was poured into 3 ml. saturated NH$_4$Cl and extracted 2×5 ml. CH$_2$Cl$_2$. The organic layers were combined, dried over Na$_2$SO$_4$ and stripped to yield a mixture of the title product, triphenylphosphine, triphenylphosphine sulfide, and mineral oil, 42.7 mg., separated by chromatography on silica gel with 1:2 ethyl acetate:hexane as eluant to yield title product as an oil, 1.3 mg., $^1$H-nmr (CDCl3) delta (ppm) 5.90 (dd, J=1.6, 4.2, 1H at the 5-position), 5.95–5.84 (m, 1H), 5.36 (s, 1H at the 2-position), 5.40–5.26 (m, 2H), 4.69 (dd, J=1.4, 5.7, 2H), 3.90 (dd, J=4.2, 16.4, 1H), 3.48 (dd, J=1.7, 16.4, 1H); tlc Rf 0.2 (1:2 ethyl acetate:hexane).

Method B

Title product of the preceding Example (35.67 mg., 0.13 mmol) in 0.5 ml. tetrahydrofuran was added to a slurry of sodium hydride (5.1 mg., 0.13 mmol) and 3.4 mg. mineral oil in 0.5 ml. tetrahydrofuran stirring at −30° C. After 30 minutes the reaction mixture was quenched and title product isolated according to Method A above.

Method C

Triphenylphosphine (52.7 mg, 0.20 mmol) was placed under nitrogen. Title product of the preceding Example (54.76 mg., 0.20 mmol) was dissolved in 1 ml. of tetrahydrofuran, added to the triphenylphosphine by syringe and the mixture cooled to 0°–5°. Potassium t-butoxide (1 ml. of 0.20M in tetrahydrofuran, freshly prepared in a dry box) was then added slowly via syringe. After 10 minutes, the mixture was quenched into 5 ml. saturated NH$_4$Cl, extracted with 2×5 ml. CH$_2$Cl$_2$, and the CH$_2$Cl$_2$ layer separated, dried over Na$_2$SO$_4$ and stripped to yield 94 mg. of crude product which was flash chromatographed on silica gel with 1:2 ethyl acetate:hexane as eluant. The resulting partially purified product was taken up in 1 ml. isopropyl ether, solid byproduct (18 mg.) recovered by filtration, and title product (28 mg.) recovered from the mother liquor by repeat chromatography on silica gel.

EXAMPLE 3

Allyl 6R,7S-4-Thioxo-7-[1R-1-(t-butyldimethylsilyloxy)ethyl]-1-aza-3,5-dithiabicyclo[4.2.0]octan-8-one-2-carboxylate

Method A

The 1:1 diastereomeric title product of Preparation 8 (30.3 mg., 0.057 mmol) was refluxed in 7 ml. CH$_3$CN for 17 hours, cooled, stripped, and chromatographed on silica gel with 1:6 ethyl acetate:hexane as eluant to yield title product as an oil, 19.5 mg.; tlc Rf 0.4 (1:5 ethyl acetate:hexane); $^1$H-nmr (CDCl$^3$) delta (ppm) 5.95–5.82 (m, 1H), 5.82 (s, 1H), 5.48 (d, J=1.6, 1H), 5.40–5.30 (m, 2H), 4.71–4.67 (m, 2H), 4.36–4.28 (m, 1H), 3.43 (dd, J=4.6, 1.7, 1H), 1.29 (d, J=6.2, 3H), 0.86 (s, 9H), 0.09 (s, 3H), 0.07 (s, 3H).

Method B

The 1:1 diastereomeric title product of Preparation 8 (1.0 g., 1.90 mmol) was thoroughly dried by taking up twice in dry benzene and stripping, and finally dried under high vacuum for 1 hour. HPLC grade CH$_3$CN (0.01% H$_2$O content, 95 ml., and 2.5 cc of molecular sieves were added and the mixture refluxed 16 hours, cooled, filtered, stripped and chromatographed with 1:6 ethyl acetate:hexane as eluant to yield 0.457 g. of title product; tlc Rf 0.5 (1:6 ethyl acetate:hexane); $^1$H-nmr as for Method A immediately above.

Method C

The entire product of Preparation 9 was taken into 5 ml. CH$_3$CN and warmed to 47° C. for 2 hours and then 62° C. for 1 hour. The reaction mixture was stripped and the residue chromatographed on silica gel, eluting first with 1:4 ethyl acetate:hexane and then with 1:2 ethyl acetate:hexane. The desired product was in the fractions eluted with the 1:4 eluant, 56 mg., tlc Rf 0.75 (1:2 ethyl acetate:hexane). Later fractions gave the desilyated product, 49 mg., tlc Rf 0.3 (1:2 ethyl acetate:hexane), indicating that greater yields can be attained by better maintaining anhydrous conditions.

EXAMPLE 4

Allyl 2S,5R,6S-3-Thioxo-6-[1R-(t-butyldimethylsilyloxy)ethyl]-1-aza-4-thiabicyclo[3.2.0]heptan-7-one-2-carboxylate or Allyl 3S,5R,6S-6-[1R-(t-butyldimethylsilyloxy)ethyl]-2-thioxopenam-3-carboxylate

Method A

The product of the preceding Example (12.5 mg., 0.029 mmol) was dissolved in 1 ml. tetrahydrofuran under N$_2$ and cooled to 0° C. Potassium t-butoxide (0.078 ml. of 0.385M in tetrahydrofuran) was added dropwise. After 3 minutes, the mixture was quenched with an equal volume of saturated NH$_4$Cl, then diluted with 4 ml. each of CH$_2$Cl$_2$ and H$_2$O. The aqueous layer was separated and extracted with 4 ml. fresh CH$_2$Cl$_2$. The organic layers were combined, dried over Na$_2$SO$_4$ and stripped to yield title product as an oil, 8.2 mg.; $^1$H-nmr (CDCl$_3$) delta (ppm) 5.96–5.80 (m, 1H), 5.86 (d, J=1.2, 1H), 5.32 (s, 1H), 5.37–5.25 (m, 2H), 4.67–4.64 (m, 2H), 4.40–4.31 (m, 1H), 3.63 (dd, J=4.0, 1.7, 1H), 1.28 (d, J=6.2, 3H), 0.87 (s, 9H), 0.08 (s, 3H), 0.07 (s, 3H); identical with the known material previously identified as a low melting solid by Leanza et al., cited above.

Method B t-Butanol (1 ml., freshly distilled from CaH) was combined with 35.4 ml. dry tetrahydrofuran and cooled to −78° C. n-Butyllithium (6.63 ml. of 1.6M in hexane) was added and the mixture warmed to 0° C. to yield a 0.3M solution of lithium t-butoxide. The product of the preceding Example (59 mg., 0.136 mmol) was dissolved in 4.5 ml. dry tetrahydrofuran and cooled to 0° C. Lithium t-butoxide (0.454 ml. of the above 0.3M solution, 0.136 mmol) was added via syringe over 2 minutes. After stirring 2 more minutes, the reaction was quenched with an equal volume of saturated NH$_4$Cl and further isolated according to Method A immediately above. The resulting product was chromatographed on silica gel using 1:49 ethyl acetate:hexane as eluant to yield purified title product, 33 mg.; identical with the product of Method A immediately above.

Method C

The product of the preceding Example (34 mg., 0.079 mmol) was dissolved in 2.6 ml. of dry tetrahydrofuran, stirred and cooled to 0° C. under N$_2$. Lithium hexamethyldisilazide (0.085 ml. of 1M solution in tetrahydrofuran, 0.085 mmol) was added by syringe. After 20 minutes of stirring, the reaction mixture was transferred into 3 ml. saturated NH$_4$Cl and extracted with 6 ml. CH$_2$Cl$_2$. The organic layer was separated, dried and stripped to an oil (36 mg.). The latter was chromatographed on silica gel to yield purified title product, 19 mg., identical with the product of Methods A and B immediately above.

EXAMPLE 5

6S-(1R-(t-butyldimethylsilyloxy)ethyl)-2-ethylthio-2-penem-3-carboxylate

The product of the preceding Example (8.2 mg., 0.020 mmol), diisopropylethylamine (Hunig's base; 0.020 ml., 0.115 mmol) and ethyl iodide (0.032 ml., 0.40 mmol) were combined under N$_2$ at 0° C. in 1 ml. tetrahydrofuran, allowed to warm to ambient temperature, stirred for 14 hours, stripped and the residue chromatographed on silica gel with 1:6 ethyl acetate:hexane as eluant to yield title product as a white solid, 2.9 mg.; tlc Rf 0.4 (1:5 ethyl acetate:hexane). $^1$M-nmr (CDCl$_3$) delta (ppm) 5.90 (m, 1H), 5.58 (s, 1H), 5.38 (bd, J=17.2, 1H), 5.20 (bd, J=10.5, 1H), 4.70 (m, 2H), 4.21 (m, 1H), 3.65 (dd, J=5.0, 1.6, 1H), 2.96 (m, 2H), 1.35 (t, J=7.4, 3H), 1.23 (d, J=6.2, 3H), 0.85 (s, 9H), 0.06 (s, 6H).

Title product is desilylated by treatment with tetrabutylammonium fluoride in tetrahydrofuran in the presence of acetic acid according to the method of Hayashi et al., Chem. Pharm. Bull. 29, pp. 3158–3172 (1981) to yield known allyl 6S-(1R-1-hydroxyethyl)2-ethylthio-2-penem-3-carboxylate, previously employed as an intermediate in the synthesis of 6S-(1R-1- hydroxyethyl)-2-ethylthio-2-penem-3-carboxylic acid (Sch 29482) by Ganguly et al., J. Antimicrob. Chemotherapy 9, Supplement C, pp. 1-6, (1982).

PREPARATION 1

4-(t-Butylthio(thiocarbonyl)thio)-2-azetidinone

Method A

4-Acetoxy-2-azetidinone (0.44 g., 3.4 mmol) and sodium t-butyl trithiocarbonate (0.64 g., 3.4 mmol) were combined in 15 ml. ethanol and stirred under $N_2$ for 20 minutes. The reaction mixture was stripped and the residue partitioned between 5 ml. each of $H_2O$ and $CH_2Cl_2$. The organic layer was separated, washed $1 \times 5$ ml. $H_2O$ and $1 \times 5$ ml. saturated brine, dried over $Na_2SO_4$, stripped to a semisolid oil (0.59 g.), and combined with 0.38 g. of like product prepared in like manner in 15 ml. of acetone from 0.31 g. (2.4 mmol) of the azetidinone. The combined crude products were chromatographed on silica gel, using as eluant 1:1 hexane:$CH_2Cl_2$ initially containing 1% methanol and finally 2% methanol, to produce solid title product, 0.95 g.; tlc Rf 0.6 (1:19 methanol:$CH_2Cl_2$); $^1$H-nmr (CDCl$_3$) delta (ppm) 6.62 (bs, 1H), 5.45 (dd, J=5.3, 2.6, 1H), 3.43 (ddd, J=15.3, 5.3, 2.0, 1H), 3.43 (ddd, J=15.3, 2.6, 1.3, 1H), 1.61 (s, 9H).

Method B

4-Acetoxy-2-azetidinone (0.21 g., 1.63 mmol) and sodium t-butyl trithiocarbonate (0.286 g., 1.5 mmol) were dissolved in 16 ml. $H_2O$. Precipitation of product began almost immediately. After 20 minutes title product was recovered by filtration and dried in high vacuum, 243 mg.; mp. 113°-116° C.

PREPARATION 2

Allyl Glyoxylate

Diallyl tartrate (17.9 g., 0.078 mol) was dissolved in 389 ml. of ether and cooled to 0° C. With stirring, solid periodic acid (35.46 g., 2 molar equivalents) was added and the mixture stirred for 4 hours, then washed $3 \times 150$ ml. saturated $Na_2S_2O_3$, dried over $Na_2SO_4$ and stripped to yield title product as an oil, 8.27 g., tlc Rf 0.4 (3:2 ethyl acetate:hexane).

PREPARATION 3

Allyl 2-Hydroxy-2-[4-(t-butylthio(thiocarbonyl)thio)-2-azetidinon-1-yl]acetate Allyl glyoxylate (0.96 g., 8.4 mmol) and 4-[t-butylthio(thiocarbonyl)thio]-2-azetidinone (0.95 g., 4.0 mmol) were combined in 40 ml. benzene under $N_2$ and refluxed for 20 hours employing a Dean-Stark trap charged with 4A type molecular sieves. Additional allyl glyoxylate (0.87 g., 7.7 mmol) was then added and refluxing continued for 24 hours. The reaction mixture was then stripped to an oil which was chromatographed on silica gel with 2:1 hexane:ethyl acetate as eluant to yield purified title product, 1.00 g.; tlc Rf 0.5 (1:1 hexane:ethyl acetate); $^1$H-nmr (CDCl$_3$) delta (ppm) 5.95 and 5.84 (2dd, J=5.4, 2.7 and J=5.3, 2.6, 1H), 6.01-5.82 (m, 1H), 5.48 and 5.27 (2d, J=8.4 and 7.8, 1H), 5.41-5.28 (m, 2H), 4.75 and 4.72-4.66 (d, J=6.0 and m, 2H), 4.01 and 3.87 (2d, J=8.4 and 7.9, 1H), 3.58 and 3.57 (2dd, J=15.7, 5.4 and 15.6, 5.5, 1H), 3.14 and 3.10 (2dd, J=15.6, 2.7 and 15.7, 2.6, 1H), 1.61 (s, 9H), reflecting two racemic pairs.

This preparation was repeated on 6.83 g. (0.029 mol) of the azetidinone and 6.63 g. (2.0 molar equivalents) of the glyoxylate, refluxing for 48 hours without further addition of glyoxylate and chromatographing with 1:2 ethyl acetate:hexane as eluant to yield 10.2 g. of title product having the same physical properties noted immediately above.

PREPARATION 4

Allyl 2-Chloro-2-[4-(t-butylthio(thiocarbonyl)thio)-2-azetidinon-1-yl]acetate

Method A

The product of the preceding Preparaton (0.10 g., 0.29 mol) and triethylamine (0.2 ml., 1.4 mmol) were dissolved in 2 ml. $CH_2Cl_2$ and cooled to 0° C. Mesyl chloride (0.033 ml., 0.43 mmol) was added and the mixture stirred at 0° C. for 20 minutes, then washed with 2 ml. $H_2O$, 2 ml. saturated $NaHCO_3$ and 2 ml. saturated NaCl, dried over $Na_2SO_4$ and stripped to an oil, 0.10 g., which was chromatographed on silica gel with 1:4 ethyl acetate:hexane as eluant to yield title diastereomeric racemic products in slightly greater than one to one ratio, 0.08 g.; tlc Rf 0.7 (1:19 $CH_3OH$:$CH_2Cl_2$, 0.6 (2:5 ethyl acetate:hexane); $^1$H-nmr (CDCl$_3$) delta (ppm), reflecting the two racemic pairs, 6.09 and 6.02 (2s, 1H), 6.04 and 5.98 (2dd, J=5.3, 2.6 and J=5.5, 2.7, 1H), 6.00-5.84 (m, 1H), 5.41-5.28 (m, 2H), 4.75-4.67 (m, 2H), 3.68 (dd, J=16.1, 5.6, 1H), 3.18 and 3.14 (2dd, J=16.1, 2.9 and J=16.0, 2.6, 1H), 1.6 (s, 9H); ir 1805, 1760 cm$^{-1}$.

Method B

The product of the preceding Preparation (1.0 g., 2.86 mmol) was dissolved in 15 ml. dry tetrahydrofuran, stirred under $N_2$, and cooled to 0° C. Triethylamine (0.479 ml., 1.2 molar equivalents) and then $SOCl_2$ (0.251 ml., 1.2 molar equivalents) were added, the latter over about 5 minutes. After stirring an additional 35 minutes at 0° C., the reaction mixture was poured into 20 ml. saturated $NaHCO_3$. Most of the tetrahydrofuran was removed in vacuo and the aqueous residue extracted $2 \times 30$ ml. $CH_2Cl_2$. The $CH_2Cl_2$ extracts were washed with saturated brine, dried over $Na_2SO_4$, stripped and the residue chromatographed on silica gel using 1:3 ethyl acetate:hexane as eluant, 0.756 g.; identical with the product of Method A above.

PREPARATION 5

Allyl 2-Bromo-2-[4-(t-butylthio(thiocarbonyl)thio-2-azetidinon-1-yl]acetate

The product of Preparation 3 (0.135 g., 0.386 mmol) was dissolved in 4 ml. of tetrahydrofuran and triethylamine (0.22 ml., 0.156 g., 1.54 mmol) was added. The mixture was cooled to 0° C. and $SOBr_2$ (0.060 ml., 0.16 g., 0.77 mmol) then added. After stirring 1.5 hours at 0° C., the reaction mixture was diluted with 8 ml. ethyl acetate, washed with $2 \times 6$ ml. saturated $NaHCO_3$, $1 \times 6$ ml. $H_2O$ and $1 \times 6$ ml. saturated brine, dried over $Na_2SO_4$, and stripped to an oil (0.168 g.) containing the title product. The latter was used without further purification in further processing. $^1$H-nmr (CDCl$_3$) delta (ppm) 6.23-5.80 (m, 3H), 5.40-5.20 (m, 2H), 4.80-4.58 (m, 2H), 3.72-3.5 (m, 1H), 3.20-3.00 (m, 1H), 1.60 (s, 9H).

PREPARATION 6

3S,4R-4-[t-Butylthio(thiocarbonyl)thio]-3[1R-1-(t-butyldimethylsilyloxy)ethyl]-2-azetidinone 3R,4R-4-Acetoxy-3-[1R-1-(t-butyldimethylsilyloxy)ethyl]-2-azetidinone (5 g., 0.0174 mol) was dissolved in 150 ml. absolute ethanol and cooled to 0° C. Carbon disulfide (0.523 ml., 0.0087 mol) and then sodium t-butyl trithiocarbonate (3.28 g., 0.0174 mol) in 50 ml. ethanol were added. After stirring 45 minutes, the reaction mixture was stripped, the residue taken up in 100 ml. ethyl acetate, washed 1×100 ml. $H_2O$ and 1×100 ml. brine, dried ($Na_2SO_4$) and stripped to a pasty solid. The latter was dried in high vacuum, slurried in minimal hexane at 0° C. and filtered to yield a first crop of title product, 3.60 g. The mother liquor was stripped and slurried in minimal hexane to yield a second crop of equally pure title product, 0.49 g.; tlc Rf 0.6 (1:2 ethyl acetate:hexane); $^1$H-nmr ($CDCl_3$) delta (ppm) 6.57 (bs, 1H), 5.58 (d, J=2.6, 1H), 4.28 (m, 1H), 3.20 (m, 1H), 1.63 (s, 9H), 1.20 (d, J=6.3, 3H), 0.88 (s, 9H), 0.07 (s, 6H).

PREPARATION 7

Allyl 2R- and 2S-2-Hydroxy-2-[3S,4R-4-(t-butylthio(thiocarbonyl))thio)-3-(1R-1-(t-butyldimethylsilyloxy)ethyl)-2-azetidinon-1-yl]acetate Using the method of Preparation 3, with 1:5 ethyl acetate:hexane as eluant on chromatography, the product of the preceding Preparation (86.4 mg., 0.20 mmol) was converted to present title product. There was obtained 21.9 mg. of less polar diastereomer; tlc Rf 0.5 (1:2 ethyl acetate:hexane); $^1$H-nmr ($CDCl_3$) delta (ppm) 6.14 (d, J=3.0, 1H), 5.89 (m, 1H), 5.49 (bs, 1H), 5.30 (m, 2H), 4.63 (m, 2H), 4.26 (m, 1H), 3.34 (dd, J=4.3, 3.0, 1H), 1.62 (s, 9H), 1.19 (d, J=6.0, 3H), 0.85 (s, 9H), 0.05 (s, 3H), 0.04 (s, 3H); 17.6 mg. of mixed fractions; and 57.1 mg. of the more polar diastereomer; tlc Rf 0.45 (1:2 ethyl acetate:hexane); $^1$H-nmr ($CDCl_3$) delta (ppm) 6.06 (d, J=2.7, 1H), 5.92 (m, 1H), 5.30 (m, 2H), 5.18 (s, 1H), 4.73 (m, 2H), 4.23 (m, 1H), 3.29 (m, 1H), 1.61 (s, 9H), 1.21 (d, J=6.1, 3H), 0.85 (s, 9H), 0.05 (s, 3H), 0.03 (s, 3H).

PREPARATION 8

1:1 Allyl 2R- and 2S-2-Chloro-2-[3S,4R-4-(t-butylthio(thiocarbonyl)thio)-3-(1R-1-(t-butyldimethylsilyloxy)ethyl)-2-azetidinon-1-yl]acetate Either diastereoisomeric product of the preceding Preparation gave a similar mixture of present title products. The more polar product of the preceding Preparation (57.1 mg., 0.11 mmol) and triethylamine (0.062 ml., 0.45 mmol) were dissolved in tetrahydrofuran (3 ml.) at 0° C. $SOCl_2$ (0.016 ml., 0.22 mmol) was added via syringe. After 45 minutes, the reaction mixture was quenched with an equal volume of saturated $NaHCO_3$ (note gas evolution). The quenched mixture was extracted 3×5 ml. $CH_2Cl_2$ and the organic layers were combined, dried over $Na_2SO_4$ and stripped to yield crude title product as an oil, 56.8 mg.; $^1$H-nmr indicated some predominance of one diastereomer. By the same method the less polar isomer (21.9 mg., 0.043 mmol) was converted to a similar crude product mixture, 24.3 mg.; $^1$H-nmr indicated some predominance of the other diastereomer. The two crude products were combined and chromatographed on silica gel to yield purified, title 1:1 product as an oil, 56.2 mg.; tlc Rf 0.4 (1:6 ethyl acetate:hexane); $^1$H-nmr ($CDCl_3$) delta (ppm), reflecting 1:1 diastereomeric product mixture, 6.40 and 6.30 (2d, J=3.1 and d, J=2.8, 1H), 6.11 and 5.89 (2s, 1H), 6.00–5.85 (m, 1H), 5.42–5.27 (m, 2H), 4.72 and 4.65 (d, J=5.9 and bd, J=6, 2H), 4.32–4.23 (m, 1H), 3.42–3.36 (m, 1H), 1.64 (s, 9H), 1.24 and 1.22 (d, J=6.2 and d, J=6.2, 3H), 0.88 and 0.86 (2s, 9H), 0.08 and 0.07 (2s, 3H), 0.06 and 0.05 (2s, 3H).

PREPARATION 9

1:1 Allyl 2R- and 2S-2-Bromo-2-[3S,4R-4-(t-butylthio(thiocarbonyl)thio)-3-(1R-1-(t-butyldimethylsilyloxy)ethyl)-2-azetidinon-1-yl]acetate The product of Preparation 7 (0.261 g., 0.512 mmol) was dissolved in 5 ml. dry tetrahydrofuran, cooled to −10° C., and triethylamine (0.10 ml., 0.717 mmol) and then $SOBr_2$ (0.048 ml., 0.614 mmol) were added. After 15 minutes at −10° C., the mixture was poured into 5 ml. each of $CH_2Cl_2$ and $H_2O$. The organic layer was separated, washed with water and saturated brine, dried over $Na_2SO_4$ and stripped to yield title product as an oil; tlc Rf 0.28 and 0.32 (1:4 ethyl acetate:hexane); $^1$H-nmr ($CDCl_3$) delta (ppm), reflecting a mixture of diastereoisomers, 6.32 (m, 1H), 6.20 and 6.07 (2s, 1H), 5.92–5.79 (m, 1H), 5.38–5.21 (m, 2H), 4.66–4.58 (m, 2H), 4.28–4.18 (m, 1H), 3.32 (m, 1H), 1.60 (s, 9H), 1.20–1.16 (m, 3H), 0.82 (s, 9H), 0.04 (s, 6H).

We claim:

1. A process for the preparation of a compound of the formula

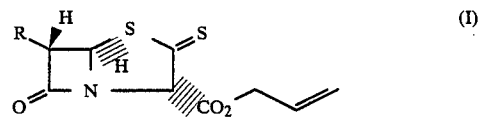

wherein R is hydrogen or

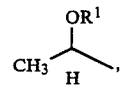

and $R^1$ is t-butyldimethylsilyl which comprises reacting a compound of the formula

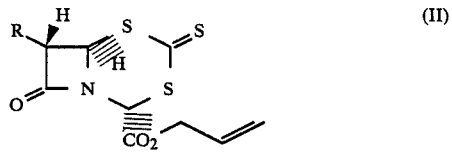

with substantially one equivalent of a strong, anhydrous base of low nucleophilicity which is an alkali metal hydride, t-butoxide or hexamethyldisilazide, with or without the presence of triphenylphosphine, in a reaction inert solvent at a temperature in the range from about −50° C. to about 10° C.

2. A process of claim 1 wherein R is hydrogen.

3. A process of claim 1 wherein R is $$\underset{CH_3}{\overset{OR^1}{\bigwedge}}\underset{H}{\overset{}{\diagdown}}.$$

4. A process of claim 1 wherein the solvent is tetrahydrofuran.

5. A proces of claim 1 wherein the base is sodium hydride.

6. A process of claim 1 wherein the base is sodium hydride in the presence of substantially one equivalent of triphenylphosphine.

7. A process of claim 1 wherein the base is potassium or lithium t-butoxide.

8. A process of claim 1 wherein the base is lithium hexamethyldisilazide.

9. A process of claim 1 which further comprises preparation of the compound of the formula (II) from a compound of the formula (III)

10. A process for the preparation of a compound of the formula (II)

wherein R is hydrogen or $$\underset{CH_3}{\overset{OR^1}{\bigwedge}}\underset{H}{\overset{}{\diagdown}},$$

and $R^1$ is t-butyldimethylsilyl, from a compound of the formula (III)

wherein R is as defined above and X is bromo or chloro, which comprises either:

(a) reacting said compound of the formula (III) with sodium iodide in a reaction inert solvent at 0°–35° C.; or (b) reacting said compound of the formula (III) in a reaction inert solvent, by warming at 25°–80° C. when X is bromo, or at 60°–100° C. when X is chloro.

11. A process of claim 10 wherein the solvent comprises acetonitrile.

12. A process of claim 10 wherein X is chloro.

13. A process of claim 11 wherein X is chloro.

14. A process of claim 10 wherein R is hydrogen.

15. A process of claim 11 wherein R is hydrogen.

16. A process of claim 10 wherein R is $$\underset{CH_3}{\overset{OR^1}{\bigwedge}}\underset{H}{\overset{}{\diagdown}}.$$

17. A process of claim 11 wherein R is $$\underset{CH_3}{\overset{OR^1}{\bigwedge}}\underset{H}{\overset{}{\diagdown}}.$$

18. A process of claim 10 wherein X is chloro and the process is carried out by heating the compound of the formula (III) at 75°–95° in acetonitrile.

19. A process of claim 10 wherein X is chloro and the process is carried out by contacting the compound of the formula (III) with sodium iodide in acetonitrile at ambient temperature.

20. A process of claim 10 wherein X is bromo and the process is carried out by warming the compound of the formula (III) in acetonitrile at 50°–60° C.

21. A process of claim 10 which further comprises converting the product compound of the formula (II) to a compound of the formula (I)

22. A compound having the formula (II)

wherein R is hydrogen or $$\underset{CH_3}{\overset{OR^1}{\bigwedge}}\underset{H}{\overset{}{\diagdown}},$$

and $R^1$ is t-butyldimethylsilyl.

23. The compound of claim 22 wherein R is hydrogen.

24. The compound of claim 22 wherein R is $$\underset{CH_3}{\overset{OR^1}{\bigwedge}}\underset{H}{\overset{}{\diagdown}}.$$

* * * * *